United States Patent
Sugaya et al.

(10) Patent No.: US 8,175,217 B2
(45) Date of Patent: May 8, 2012

(54) X-RAY CT APPARATUS

(75) Inventors: Yoshiaki Sugaya, Tokyo (JP); Taiga Goto, Tokyo (JP); Koichi Hirokawa, Tokyo (JP); Osamu Miyazaki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 232 days.

(21) Appl. No.: 12/742,797

(22) PCT Filed: Nov. 17, 2008

(86) PCT No.: PCT/JP2008/070843
§ 371 (c)(1),
(2), (4) Date: May 13, 2010

(87) PCT Pub. No.: WO2009/069489
PCT Pub. Date: Jun. 4, 2009

(65) Prior Publication Data
US 2010/0254509 A1 Oct. 7, 2010

(30) Foreign Application Priority Data
Nov. 28, 2007 (JP) .................. 2007-306814

(51) Int. Cl.
*A61B 6/03* (2006.01)
(52) U.S. Cl. .................. 378/16; 378/4
(58) Field of Classification Search ............... 378/4–20; 382/131; 600/425, 431
See application file for complete search history.

(56) References Cited

U.S. PATENT DOCUMENTS

| | | | | |
|---|---|---|---|---|
| 5,459,769 A | * | 10/1995 | Brown | 378/4 |
| 7,715,522 B2 | * | 5/2010 | Goto et al. | 378/16 |
| 7,945,013 B2 | * | 5/2011 | Goto et al. | 378/16 |
| 2003/0108149 A1 | | 6/2003 | Tsuyuki | |

FOREIGN PATENT DOCUMENTS

| JP | 2001-178713 | 7/2001 |
|---|---|---|
| JP | 2003-245275 | 9/2003 |

OTHER PUBLICATIONS

PTO 11-2408, Development of CT Exposure Optimization System, translation.*
Koichi Hirokawa et al., "CT Satsuei Senryo Saitekika Gijutsu no Kaihatsu", MEDIX, Mar. 10, 2006, p. 35-39, vol. 44, Hitachi, Japan.

* cited by examiner

*Primary Examiner* — Edward Glick
*Assistant Examiner* — John Corbett
(74) *Attorney, Agent, or Firm* — Cooper & Dunham LLP (57) ABSTRACT

An X-ray CT apparatus is provided with an X-ray tube current modulation pattern calculation means that calculates an X-ray tube current modulation pattern based on a 3-dimensional model of an object calculated based on a scanogram image of the object, start-up shape acquisition means that acquires a start-up shape of CT values of a predetermined region of the object or CT value time differences after injecting contrast agent into the object, time contrast curve prediction means that predicts a time contrast curve indicative of a time sequential change of contrast in a diagnostic portion of the object at each slice position at a scan time based on the acquired start-up shape of the CT values or CT value time differences, object 3-dimensional model modification means that modifies a 3-dimensional model of the object based on the predicted time contrast curve, and X-ray tube electric current modulation pattern modification means that modifies the X-ray tube electric current modulation pattern based on the modified 3-dimensional model of the object.

11 Claims, 9 Drawing Sheets

X-RAY CT APPARATUS

TECHNICAL FIELD

The present invention relates to an X-ray CT apparatus, in particular to an X-ray CT apparatus which controls X-ray tube current during scan considering image quality and exposure dose.

BACKGROUND ART

An X-ray CT apparatus irradiates an X-ray of a fan beam or cone beam (conical shape or pyramid shape) to an object to be examined, acquires projection data which is the information related to intensity of the X-ray that is transmitted through the object, and scans distribution information of X-ray absorption coefficient in the object based on the acquired projection data.

The X-ray CT apparatus acquires projection data in discrete X-ray tube positions (views). The view number per one rotation of an X-ray tube normally reaches from several hundreds to several thousands. The X-ray CT apparatus executes scanning by irradiating an X-ray while rotating an X-ray tube around the object, and acquires projection data of the view number necessary for reconstructing a piece of tomographic image (CT image).

As for the scan condition of an X-ray CT apparatus, when an X-ray tube current is constant, there are cases that radiation dosage is excessive or insufficient depending on the irradiation angle of an X-ray or an irradiation target region. In response, the technique for an X-ray CT apparatus has been proposed which is to achieve suppression of radiation dose and improvement of image quality by controlling an X-ray tube current by measuring X-ray transmission data of the object during scan in real time (for example, refer to [Patent Document 1]).

Also, a technique for an X-ray CT apparatus has been proposed which is to calculate an elliptic cross-section model of the object from scanogram projection data, and calculate an X-ray tube current value using the area and the aspect ratio of the elliptic cross-section (for example, refer to [Patent Document 2]).

Also, a technique for an X-ray CT apparatus has been proposed which is to modify an object cross-sectional model considering the weight of the object or information on injection amount and density of contrast agent in an examination using contrast agent (for example, refer to [Patent Document 3]).

Patent Document 1: JP-A-H10-309271
Patent Document 2: JP-A-2001-043993
Patent Document 3: JP-A-2005-305026

DISCLOSURE OF THE INVENTION

Problems to be Solved

However, the X-ray CT apparatus in [Patent Document 1] calculates the output of the X-ray after transmitting through the object during rotation of an X-ray tube, there is a problem that the actual control of the X-ray tube current follows the X-ray output prior to several view portions. In the X-ray CT apparatus of [Patent Document 2], since an elliptic cross-sectional model is given in advance, the X-ray tube voltage can be controlled without depending on the irradiation angle or the irradiating target region, without delay of time phase compared to [Patent Document 1]. However, while the irradiation X-ray amounts are different when the X-ray tube voltages are different, calculation of X-ray tube current modulation pattern in accordance with the X-ray tube current has not been disclosed concretely in [Patent Document 1] nor in [Patent Document 2].

In a contrast examination using an X-ray CT apparatus, density (CT value) of a diagnostic region (scan target region) changes over time. In the X-ray CT apparatus of [Patent Document 3], since the object cross-sectional model is modified based on preliminary information related to contrast agent prior to injecting of contrast agent into the object, the information related to change in concentration (CT value variation) in the diagnostic region of the object after actual injection of contrast agent can not be reflected to the modification of the object cross-sectional model, whereby making it difficult to obtain the appropriate X-ray tube current modulation pattern.

The objective of the present invention is to provide an X-ray CT apparatus, considering the above-described problems, capable of improving image quality and suppressing exposure dose by corresponding to the change of X-ray absorption coefficient over time in a contrast examination.

Means to Solve the Problem

In order to achieve the above-mentioned objective, the present invention comprises:
an X-ray source configured to irradiate an X-ray while rotating around an object to be examined;
an X-ray detector disposed facing the X-ray source having the object therebetween, and configured to detect the X-ray dose which is transmitted through the object;
image reconstruction means configured to reconstruct a tomographic image of the object based on the detected X-ray dose; and
display means configured to display the tomographic image,
and is characterized in further comprising:
X-ray tube current modulation pattern calculation means configured to calculate the X-ray tube current modulation pattern based on a 3-dimensional model of the object which is calculated based on a scanogram image of the object;
start-up shape acquisition means configured to acquire a start-up shape of the CT values or a CT value time difference at a predetermined region of the object after injecting contrast agent into the object;
time contrast curve prediction means configured to predict a time contrast curve indicating time sequential variation of contrast in a diagnostic region of the object with respect to each slice position upon scanning based on the start-up shape of the acquired CT values or CT time difference;
object 3-dimensional model modification means configured to modify the 3-dimensional model of the object based on the predicted time contrast curve; and
X-ray tube current modulation pattern modification means configured to modify the X-ray tube current modulation pattern based on the modified object 3-dimensional model.

The X-ray CT apparatus of the present invention measures variation of a CT value over time by executing monitoring scan at the position of the upstream of the diagnostic region after injecting contrast agent into the object, predicts a time contrast curve with respect to the respective slice positions upon scanning based on the start-up shape of the CT values or CT value time difference, modifies the object 3-dimensional model based on the predicted time contrast curve, modifies the X-ray tube current modulation pattern based on the modified object 3-dimensional model, and executes contrast scan of the diagnostic region.

Accordingly, the X-ray CT apparatus of the present invention is capable of setting an appropriate X-ray tube current modulation pattern considering the variation of an X-ray absorption coefficient over time due to contrast agent, while improving image quality and suppressing exposure dose in a contrast examination using an X-ray CT apparatus.

Also, it may be configured to have the standard data of a time contrast curve and to modify the standard data of the time contrast curve based on the irradiation condition of an X-ray or information related to the object, so as predict the time contrast curve. The irradiation condition of an X-ray is, for example, the X-ray tube voltage to be applied to an X-ray source or scan protocol. Information related to an object is, for example, physique information such as physical attribute or weight. By such method, a time contrast curve can be predicted without executing monitoring scan.

Also, X-ray tube current value amplitude or an X-ray tube current modulation maximum value may be determined based on the X-ray tube voltage to be applied to the X-ray source. In this manner, it is possible to calculate an appropriate X-ray tube current modulation pattern in accordance with an X-ray tube current.

Effect of the Invention

In accordance with the present invention, it is possible to provide the X-ray CT apparatus capable of improving image quality as well as suppressing exposure dose by corresponding to variation of an X-ray absorption coefficient over time in a contrast examination.

BRIEF DESCRIPTION OF THE DIAGRAMS

DESCRIPTION OF REFERENCE NUMERALS

1. X-ray CT apparatus, 2: gantry, 3: patient table, 4: console, 5: top board, 6: object, 7: displayer, 8: operation device, 10: X-ray tube (X-ray source), 11: high-voltage generator, 12: slip ring, 13: collimator, 14: X-ray detector, 15: data collection circuit, 16: scanning driving unit, 17: driving frame, 18: X-ray tube voltage/current measuring device, 20: system controller, 21: table controller, 22: top-board driving device, 23: image reconstruction device, 24: storage device, 25: scan planning device, 26: TCD/TCC prediction device, 27: contrast agent injection controller, 28: exposure controller, 29: object 3-dimensional model calculation/modification device, 30: X-ray tube current modulation pattern calculation/modification device, 31: time density curve (TDC), 32: time contrast curve (TCC), 41 object 3-dimensional model, 41-1: object 3-dimensional model (before modification), 41-2: object 3-dimensional model (after modification), 51 and 52: X-ray current modulation pattern

BEST MODE FOR CARRYING OUT THE INVENTION

A preferred embodiment of the present invention will be described below referring to the attached diagrams. In the description and the attached diagrams below, the components having the same function will be appended with the same reference numerals and the repeated explanation will be omitted.

(1. Configuration of X-ray CT Apparatus 1)

First, the configuration of X-ray CT apparatus 1 will be described referring to FIG. 1 and FIG. 2.

Figure 1:
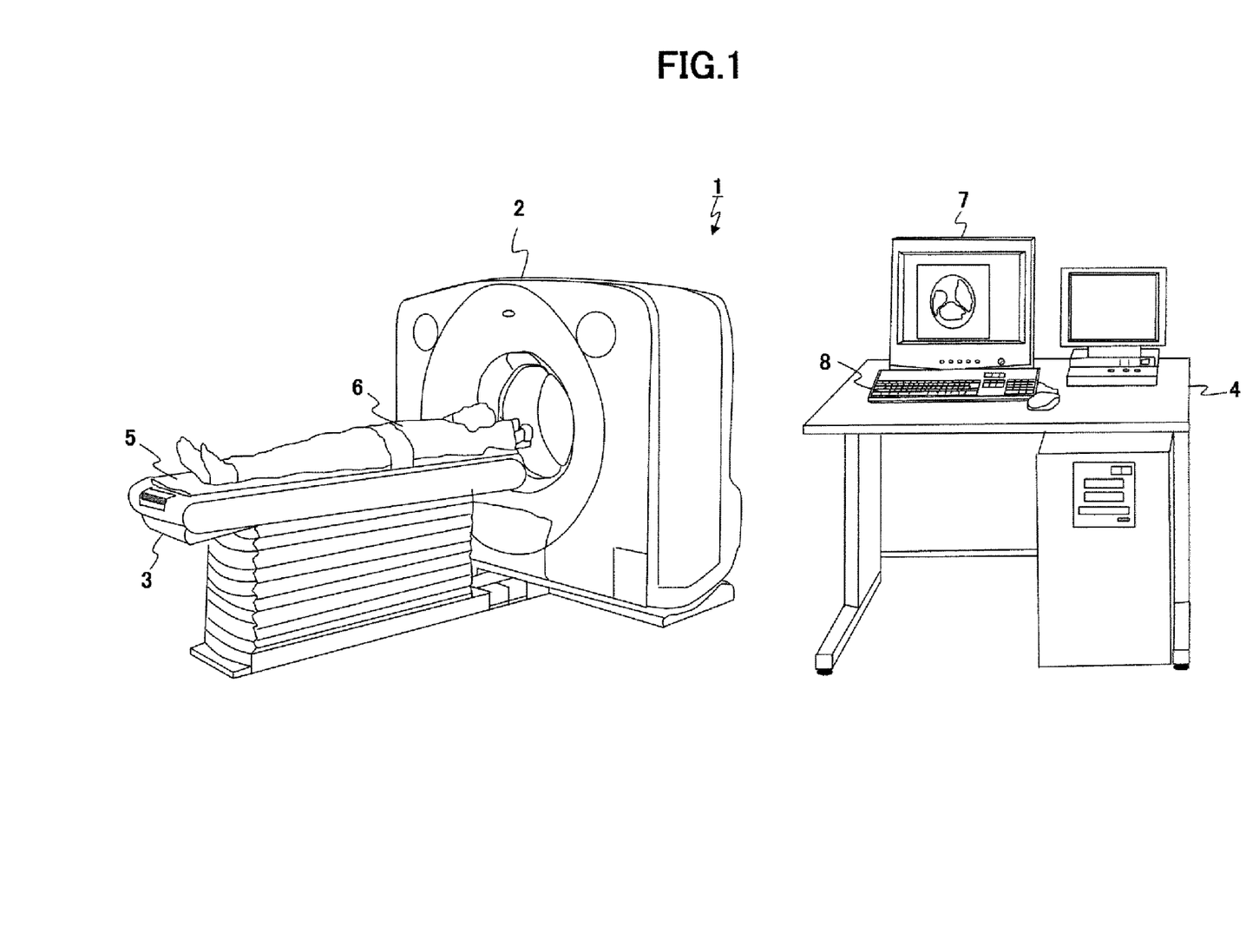
FIG. 1 is an external view showing the general configuration of X-ray CT apparatus 1.

FIG. 1 is an external view of the general configuration of X-ray CT apparatus 1.

Figure 2:
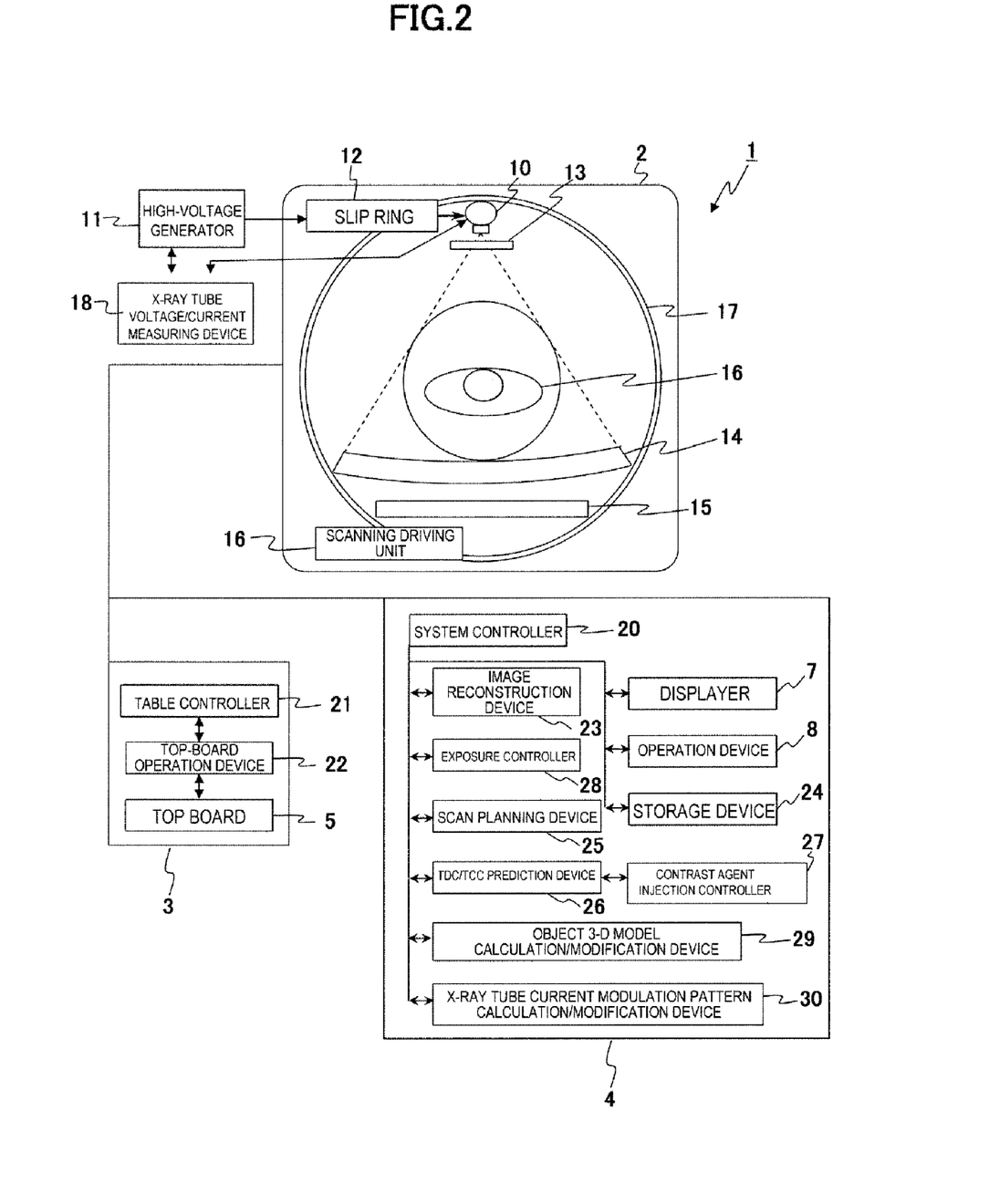
FIG. 2 is a block diagram of X-ray CT apparatus 1.

FIG. 2 is a block diagram of X-ray CT apparatus 1.

While the X-ray CT apparatus has one X-ray tube in the present embodiment, the present invention is also applicable to a multi-source type X-ray CT apparatus. Also, while there are various types of X-ray CT apparatuses such as the rotate-rotate method wherein an X-ray tube and an X-ray detector are integrated as one for irradiating wide fan beams to cover an object while rotating, the scanning electron beam method which applies an electron beam to a target electrode while electrically deflecting it, and others, the present invention is applicable to any of these X-ray CT apparatuses.

X-ray CT apparatus 1 is configured by gantry 2, patient table 3, console 4, top board 5 provided to patient table 3, displayer 7 and operation device 8. X-ray CT apparatus 1 acquires X-ray absorption coefficient distribution information of object 6 by carrying object 6 which is fixed on top board 5 on patient table 3 in gantry 2 and scanning.

Gantry 2 is configured by X-ray tube 10, high-voltage generator 11, slip ring 12, collimator 13, X-ray detector 14, data collection circuit 15, scanning driving unit 16, driving frame 17 and X-ray tube voltage/current measuring device 18.

X-ray tube 10 is an X-ray source, and irradiates an X-ray to object 6. In order to irradiate an X-ray, electric power is provided from high-voltage generator 11 to X-ray tube 10 via slip ring 12, and the X-rays are intermittently or continuously eradiated from X-ray tube 10. The X-ray tube voltage and the X-ray tube current applied and provided to X-ray tube 10 are measured by X-ray tube voltage/X-ray tube current measuring device 18 on a steady basis. High-voltage generator 11 controls the X-ray tube voltage and the X-ray tube current applied and provided to X-ray tube 10 based on the measurement result by X-ray tube voltage/current measuring device 18.

Collimator 13 irradiates the X-ray eradiated from X-ray tube 10 as an X-ray of a cone beam (conical or pyramid beam), etc. to object 6.

X-ray detector 14 detects the X-rays eradiated from X-ray tube 10 and transmitted through object 6.

Data collection circuit 15 is connected to X-ray detector 14, and collects the detection data of the individual X-ray detection elements of X-ray detector 14.

To driving frame 17, X-ray tube 10, collimator 13, X-ray detector 4 and data collection circuit 15 are provided. Driving frame 17 is rotated by the drive force transmitted from scanning driving unit 16 controlled by system controller 20. High-voltage generator 11 and X-ray tube voltage/current measuring device 18 may also be provided to driving frame 17.

Patient table 3 is configured by top board 5, table controller 21 and top-board driving device 22.

Table controller 21 controls top-board driving device 22 and controls the height and forward-backward movement of top board 5. By such function, object 6 is carried in and out of an X-ray irradiation space of gantry 2.

Console 4 is configured by displayer 7, operation device 8, system controller 20, image reconstruction device 23, storage device 24, scan planning device 25, TDC/TCC prediction device 26, contrast agent injection controller 28, exposure controller 27, exposure controller 28, object 3-dimensional model calculation/modification device 29, and X-ray tube current modulation pattern calculation/modification device 20.

Displayer 7 is connected to system controller 20, and displays reconstructed images outputted from image reconstruction device 23 or a variety of information to be handled in system controller 20.

Operation device 8 is connected to system controller 20, and is for an operator to input a variety of commands or information to system controller 20. The operator operates the X-ray CT apparatus interactively using displayer 7 and operation device 8.

System controller 20 is connected to gantry 2 and patient table 3. System controller 20 controls high-voltage generator 11, a collimator controller (not shown in the diagram), data collection circuit 15 and X-ray detector 14, and also controls table controller 21 in patient table 3.

Image reconstruction device 23 receives the data collected by data collection circuit 15 in gantry 2 under control of system controller 20, generates a scanogram image upon scanogram imaging using the scanogram projection data collected by data collection circuit 15, and reconstructs a tomographic image upon scanning using projection data of a plurality of views collected by data collection circuit 15.

Storage device 24 is connected to system controller 20, and stores the scanogram image and the tomographic image generated and reconstructed in image reconstruction device 23, various data, or programs for actualizing functions of the X-ray CT apparatus.

Scan planning device 25 is connected to system controller 20, for the operator to create a plan for scan conditions using the commands inputted from operation device 8 and the scanogram image read out from storage device 24. In concrete terms, the scanogram image read out from storage device 24 is displayed on displayer 7, and the operator specifies the slice position on the displayed scanogram using operation device 8 so as to set the slice position upon scanning. The information related to the set slice position is stored in storage device 24, and used also for planning the X-ray controlling conditions by scan planning device 25. As for the function to execute most suitable X-ray control with respect to the object of which a scanogram imaging is performed in advance, various sorts of common techniques can be used. Exposure controller 28 controls an X-ray tube current during scanning.

TCD/TCC prediction device 26 measures a time density curve (TDC) and a time contrast curve (TCC) of a diagnostic region based on the previously inputted information such as the physique or weight of the object or the information obtained by monitoring scan. To TDC/TCC prediction device 26, contrast injection controller 27 for properly injecting contrast agent is connected. Explanation on the time density curve and the time contrast curve will be described later.

Object 3-dimensional model calculation/modification device 29 calculates an object 3-dimensional model based on the scanogram projection data acquired by scanogram imaging, and modifies the object 3-dimensional model based on the predicted time contrast curve.

X-ray tube current modulation pattern calculation/modification device 30 calculates the X-ray tube current modulation pattern based on the object 3-dimensional model, and modifies the X-ray tube current modulation pattern based on the modified object 3-dimensional model.

The X-ray irradiation range of the X-ray eradiated from X-ray tube 10 is controlled by collimator 13, and the controlled X-ray is made into a fan beam or a cone beam (or pyramid beam) to be irradiated to object 6. Top-board driving device 22 and table controller 21 adjusts the scan range which is set by the operator, by controlling the position of top board 5.

The X-rays transmitted through object 6 are detected by X-ray detector 14. In the case of a multi-slice X-ray CT apparatus, X-ray detector 14 generally has a curved structure arranged with two to several hundreds of X-ray detection elements in the body-axis direction and several hundred to a thousand channels of X-ray detection elements in the body-width direction. The detection data converted into electric signals in X-ray detector 14 is transferred and A/D converted in data collecting circuit 15 referred to as DAS (Data Acquisition System), and accumulated in storage device 24 under control of system controller 20.

Image reconstruction device 23 reconstructs a tomographic image based on the accumulated collection data, and displayer 7 displays the reconstructed tomographic image. A scanogram image is generated in image reconstruction device 23 using projection data of the object 6 acquired by data collection circuit 15 upon scanogram imaging, and a tomographic image is reconstructed in image reconstruction device 23 using projection data of a plurality of views acquired by data collecting circuit upon main scanning (actual scanning) after the scanogram imaging. The scanogram image or tomographic image generated or reconstructed by image reconstruction device 23 are stored in storage device 24.

(2. Operation of X-ray CT Apparatus 1)

Next, operation of X-ray CT apparatus 1 will be described referring to FIG. 3.

Figure 3:
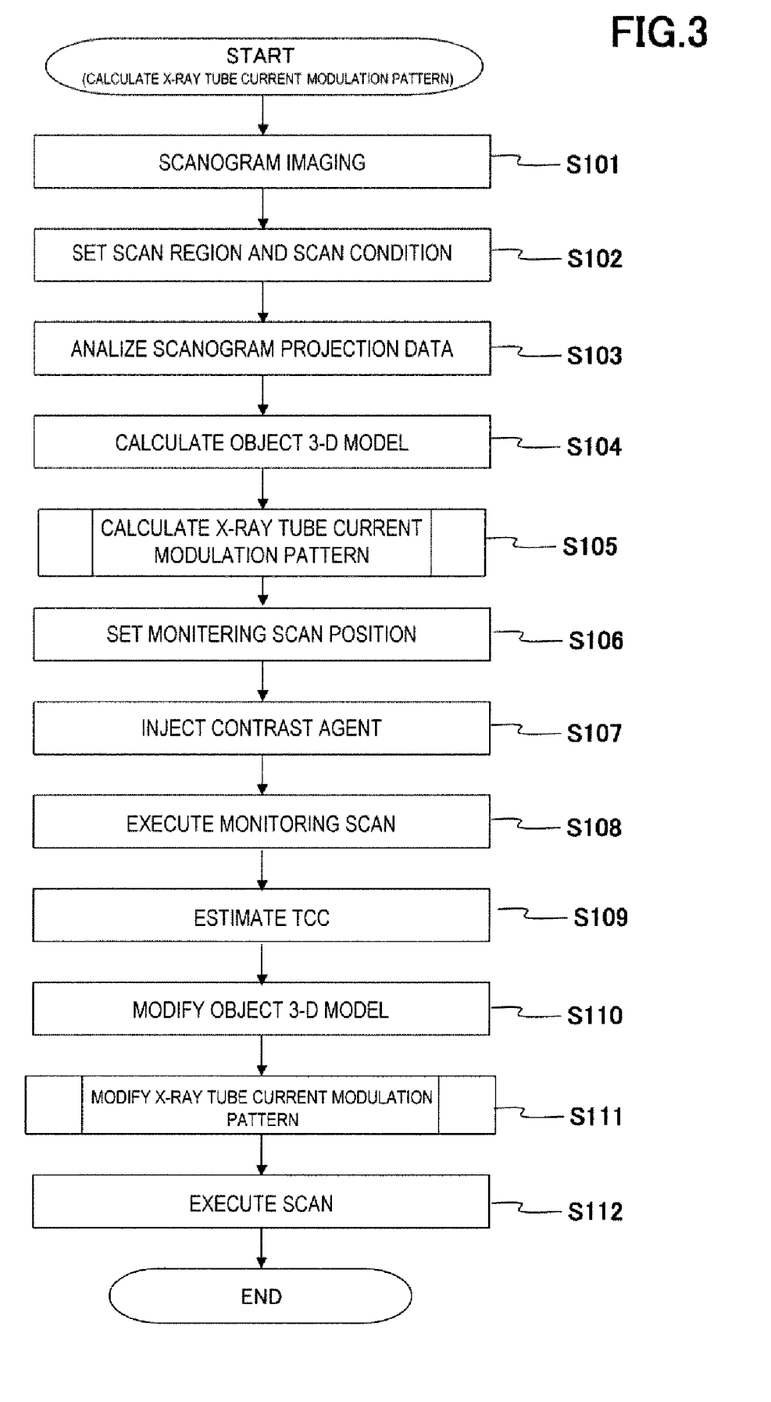
FIG. 3 is a flowchart showing operation of X-ray CT apparatus 1.

FIG. 3 is a flowchart showing the operation of X-ray CT apparatus 1.

X-ray CT apparatus 1 executes scanogram imaging of object 6, acquires scanogram projection data and generates a scanogram image (step 101). The procedure of scanogram imaging is basically the same as the one of scanning. X-ray CT apparatus 1 irradiates an X-ray to object 6 in one direction (for example, from the back to the front) without rotating X-ray tube 10, and acquires scanogram projection data by X-ray detector 14. X-ray CT apparatus 1 transfers the scanogram projection data to image reconstruction device 23 via system controller 20, generates a scanogram image and displays it on displayer 7. This scanogram image is, for example, the image of the X-ray being transmitted from the back to the front of the object viewing from one direction.

The operator sets a scan region and scan condition using operation device 8 based on the scanogram image (step 102). The scan region indicates the slice position, scan starting position and scan ending position of object 6 upon scanning.

Scan condition is, for example, moving pitch of top board 5, scan time, X-ray collimation condition, the kind of reconstruction filter function, and FOI size. X-ray CT apparatus 1 stores the set scan region and scan condition in storage device 24.

X-ray CT apparatus 1 determines slice position [z] corresponding to the tomographic scanning range of object 6 by scan planning device 25 using the set scan region and scan condition. The scan starting position and the scan ending position respectively indicates slice position [z] of the initial tomographic image and slice position [z] of the last tomographic image obtained in a series of scans.

X-ray CT apparatus 1 analyzes the scanogram projection data by scan planning device 25, and calculates an object 3-dimensional model (step 104). The object 3-dimensional model is, for example, the respective cross-sections of object 6 corresponding to slice position [z] approximated to an elliptic cross-section having the X-ray absorption coefficient equivalent to water.

X-ray CT apparatus 1 calculates an X-ray tube current modulation pattern based on the object 3-dimensional model calculated in the process of step 104 (step 105). The calculation of an X-ray tube current modulation pattern will be described later referring to FIG. 6~FIG. 9.

The operator sets slice position [$z_m$] in monitoring scan using operation device 8 based on the scanogram image (step 106). The slice position in the monitoring scan is set on the upstream in the scan direction with respect to the position of the diagnostic region. For example, in the case that the diagnostic region for a scan target is a lever, the monitoring scan target is an aorta abdominalis.

X-ray CT apparatus 1 injects contrast agent into object 6 using contrast agent injection controller 27 (step 107). X-ray CT apparatus 1 executes monitoring scan (step 108). In monitoring scan, X-ray CT apparatus 1 predicts time density curve (TDC) and time contrast curve (TCC) to be described later based on the image information obtained by the monitoring scan (step 109). X-ray CT apparatus 1 modifies the object 3-dimensional model calculated by the process in step 104 based on the time contrast curve predicted in the process of step 109 (step 110).

Figure 4:
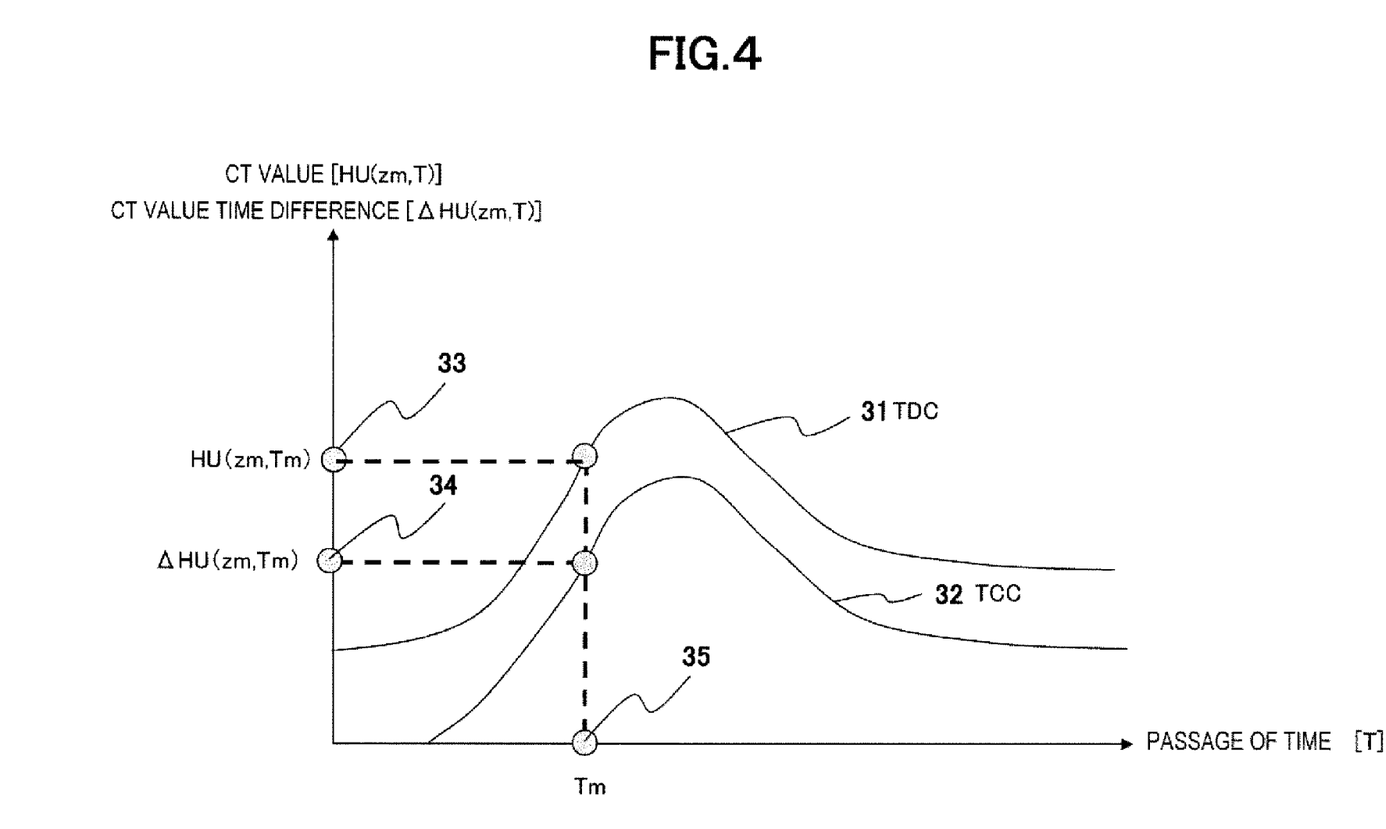
FIG. 4 is a chart showing time density curve 31 and time contrast curve 32.

FIG. 4 is a chart showing time density curve 31 and time contrast curve 32 in slice position [$z_m$] of the monitoring scan. The vertical axis indicates CT value [HU($z_m$, T)] or CT value time difference [ΔHU($z_m$, T)]. The lateral axis indicates the passage of time [T] since the injection of contrast agent into object 6.

When contrast agent is injected into object 6, the X-ray absorption coefficient increases and decreases along with passage of time. Time density curve 31 indicates time variation of a CT value in the diagnostic region (for example, a substantial portion of a lever) since the start of the contrast examination. Time contrast curve 32 is the difference wherein density of contrast agent before arrival is subtracted from time density curve 31 at the respective times, and indicates the contrast effect in the diagnostic region.

When X-ray CT apparatus 1 detects the time point (time point 35[$T_m$]) wherein the CT value or the CT value time difference measured by the monitoring scan surpasses a predetermined threshold value (threshold value 33 or threshold 34), i.e. the start-up of the CT value or the CT value time difference by injection of contrast agent, it predicts time density curve 31 based on the start-up shape of the CT value or CT value time difference. In concrete terms, the operator inputs to X-ray CT apparatus 1 in advance the object information such as physique or weight of the object and contrast agent information such as contrast agent density, contrast agent injection velocity, contrast agent injection time and contrast agent injection amount. X-ray CT apparatus 1 simulates time density curve 31 based on the object information, contrast agent information or the start-up shape of the CT value or the CT value time difference.

Time contrast curve 32 may be simulated in the same manner as time density curve 31, or calculated based on the time difference of time density curve 31. Also, as for the simulation of time density curve 31 or time contrast curve 32, a common technique (for example, refer to Aortic and hepatic contrast medium enhancement at CT: Part I. Prediction with a computer model. Radiology 1998; 207: 647-655) may be used.

Figure 5:
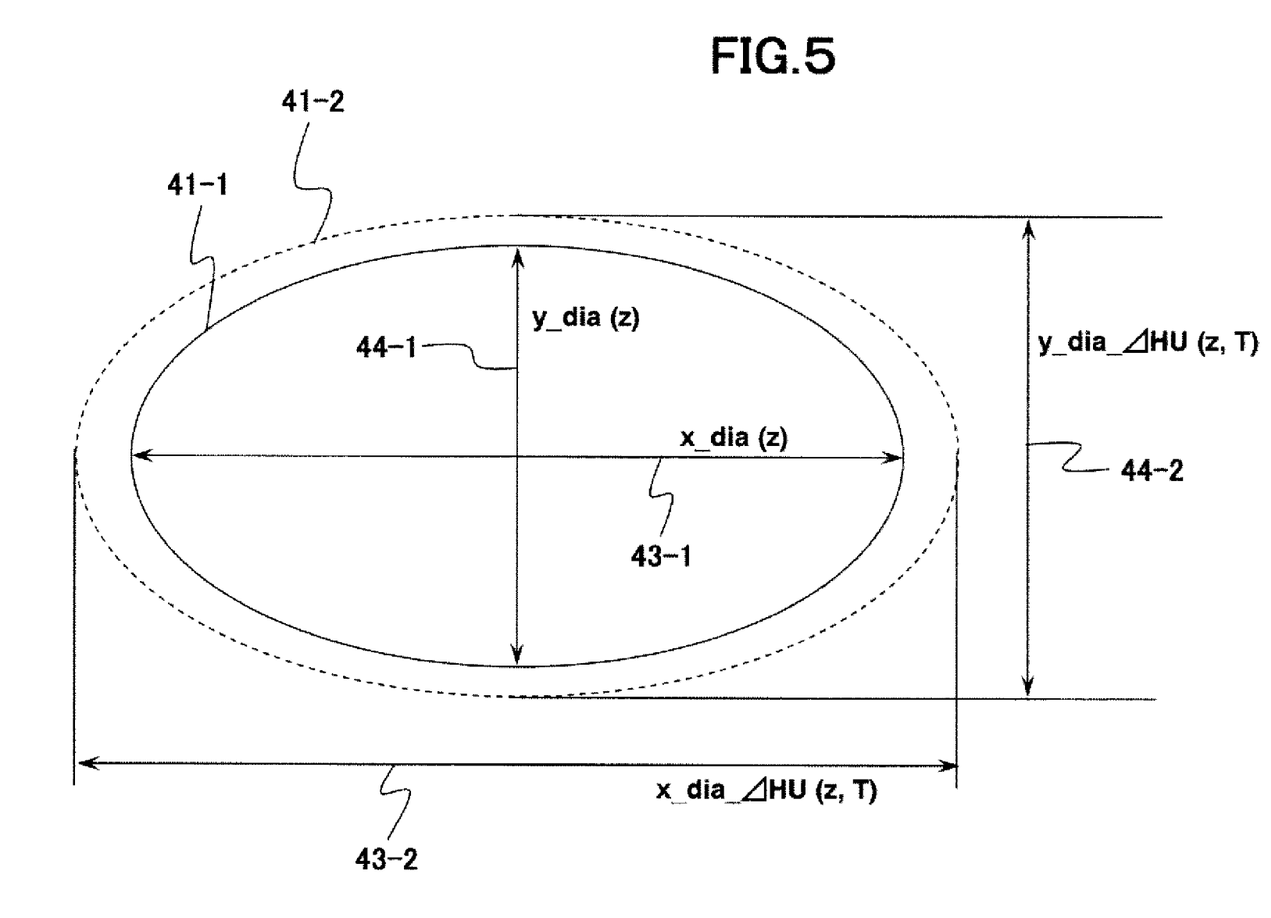
FIG. 5 is a chart showing modification of object 3-dimensional model 41.

FIG. 5 shows the modification of object 3-dimensional model 41.

Object 3-dimensional model 41-1 is the object 3-dimensional model calculated in the process of step 104. Object 3-dimensional model 41-2 is the object 3-dimensional model modified in the process of step 110.

X-ray CT apparatus 1 reads out the moving pitch of top board 5, the scan stating point and the scan ending point, and the information related to the scan time being set in the process of step 102 from storage device 24, and corresponds them to elapsed time [T] since the injection of contrast agent and the respective slice positions [z] upon scanning.

X-ray CT apparatus 1 calculates CT value time difference [ΔHU(z, T)] of slice position [z] in elapsed time [T] regarding scanning time, based on time contrast curve 32 predicted in the process of step 109. X-ray CT apparatus 1 modifies object 3-dimensional model 41 using the calculated CT value time difference. Concretely, X-ray CT apparatus 1 modifies object 3-dimensional model 41-1 to object 3-dimensional model 41-2 in accordance with [formula 1].

$$\text{x\_dia\_}\Delta HU(z, T) = \text{x\_dia}(z) * \left(1 + \frac{\Delta HU(z, T) * m}{1000}\right) \quad \text{[Formula 1]}$$

$$\text{y\_dia\_}\Delta HU(z, T) = \text{y\_dia}(z) * \left(1 + \frac{\Delta HU(z, T) * m}{1000}\right)$$

In this regard, x_dia(z): the length of long-axis 43-1 of object 3-dimensional model 41-1, y_dia(z): the length of short-axis 44-1 of object 3-dimensional model 41-1, x_dia(z)_ΔHU(z, T): the length of long-axis 43-2 of object 3-dimensional model 41-2 after modification, y_dia(z)_ΔHU(z, T): the length of short-axis 44-2 of object 3-dimensional model 41-2 after modification, and m: proportionality constant. Constant proportion [m] is the coefficient for modification, and the specific value may be stored in storage device 24 for each diagnostic region.

Returning to FIG. 3, X-ray apparatus 1 modifies the X-ray tube current modulation pattern calculated in the process of step 105 based on the object 3-dimensional model which is modified in the process of step 110 (step 111). In concrete terms, X-ray CT apparatus 1 modifies X-ray tube current attenuation coefficient [modu_ratio(z, T)] in slice position [z] of elapsed time [T] regarding a scanning time in accordance with [formula 2]. X-ray tube current attenuation coefficient indicates the X-ray tube current attenuation ratio based on the maximum X-ray tube current value in the slice position in accordance with the difference of the X-ray transmission lengths.

$$\text{modu\_ratio}(z, T) = \exp\left(-\mu_{kV} * \left(1 + \frac{\Delta HU(z, T) * m}{1000}\right) * |x\_dia\_\Delta HU(z, T) - y\_dia\_\Delta HU(z, T)|\right) \quad \text{[Formula 2]}$$

In this regard, $\mu_{kV}$: the constant set for each X-ray tube voltage.

Constant $\mu_{kV}$ is, in the case that an object 3-dimensional model is a water equivalent 3-dimensional model, the X-ray absorption coefficient of water determined by X-ray effective energy under the set X-ray tube voltage condition. The X-ray effective energy may be measured in advance, or calculated by a simulation. The X-ray effective energy in the respective X-ray tube voltages may be measured in accordance with the object model in variety of sizes or a material, and the X-ray absorption coefficient for each X-ray effective energy may be stored in storage device 24.

X-ray CT apparatus 1 executes scanning of a diagnostic region based on the X-ray tube current modulation pattern modified in the process of step 111, and displays the tomographic image of object 6 into which contrast agent is injected on displayer 7 (step 112).

In accordance with the above-described process, X-ray CT apparatus 1 calculates an object 3-dimensional model by analyzing scanogram projection data, and calculates an X-ray tube current modulation pattern based on the calculated object 3-dimensional model. The X-ray CT apparatus 1, after injecting contrast agent into object 6, executes monitoring scan at the position in the upstream of a diagnostic region, and acquires a start-up shape of the CT values or the CT value time difference. X-ray CT apparatus 1 predicts time density curve 31 or time contrast curve 32 based on the start-up shape of the acquired CT values or the CT value time difference. X-ray CT apparatus 1 modifies the object 3-dimensional model in the respective slice positions upon scanning based on the predicted time contrast curve 32, modifies the X-ray tube current modulation pattern based on the modified object 3-dimensional model, and executes contrast scan of the diagnostic region.

In concrete terms, modification of an object 3-dimensional model and the X-ray tube current modulation pattern is executed by performing calculation using x_dia(z)_ΔHU(z, T), y_dia(z)_ΔHU(z, T) and modu_ratio(z, T) of [formula 1] and [formula 2] in place of x_dia(z), y_dia(z) and modu_ratio (z) of [formula 3]~[formula 8] to be described later respectively.

In this manner, X-ray CT apparatus 1 is capable of setting an appropriate X-ray tube current modulation pattern considering time variation of X-ray absorption coefficient due to contrast agent, and achieving improvement of image quality and suppression of exposure dose in a contrast examination using an X-ray CT apparatus.

While time contrast curve 32 is predicted by executing monitoring scan after injecting contrast agent into object 6 in the above-described embodiments, for example, desired time contrast curve 32 wherein the data of a person having the standard physique of object 6 is acquired may be set in advance and stored in storage device 24. In this manner, a time contrast curve may be predicted without executing monitoring scan. Also, time contrast curve 32 predicted considering object information such as physique or weight of object 6 or scan condition such as scan protocol or an X-ray tube voltage may be appropriately changed.

(3. Calculation of X-ray Tube Current Modulation Pattern)

Next, calculation of X-ray tube current modulation pattern (step 105 of FIG. 3) will be described referring to FIG. 6.

Figure 6:
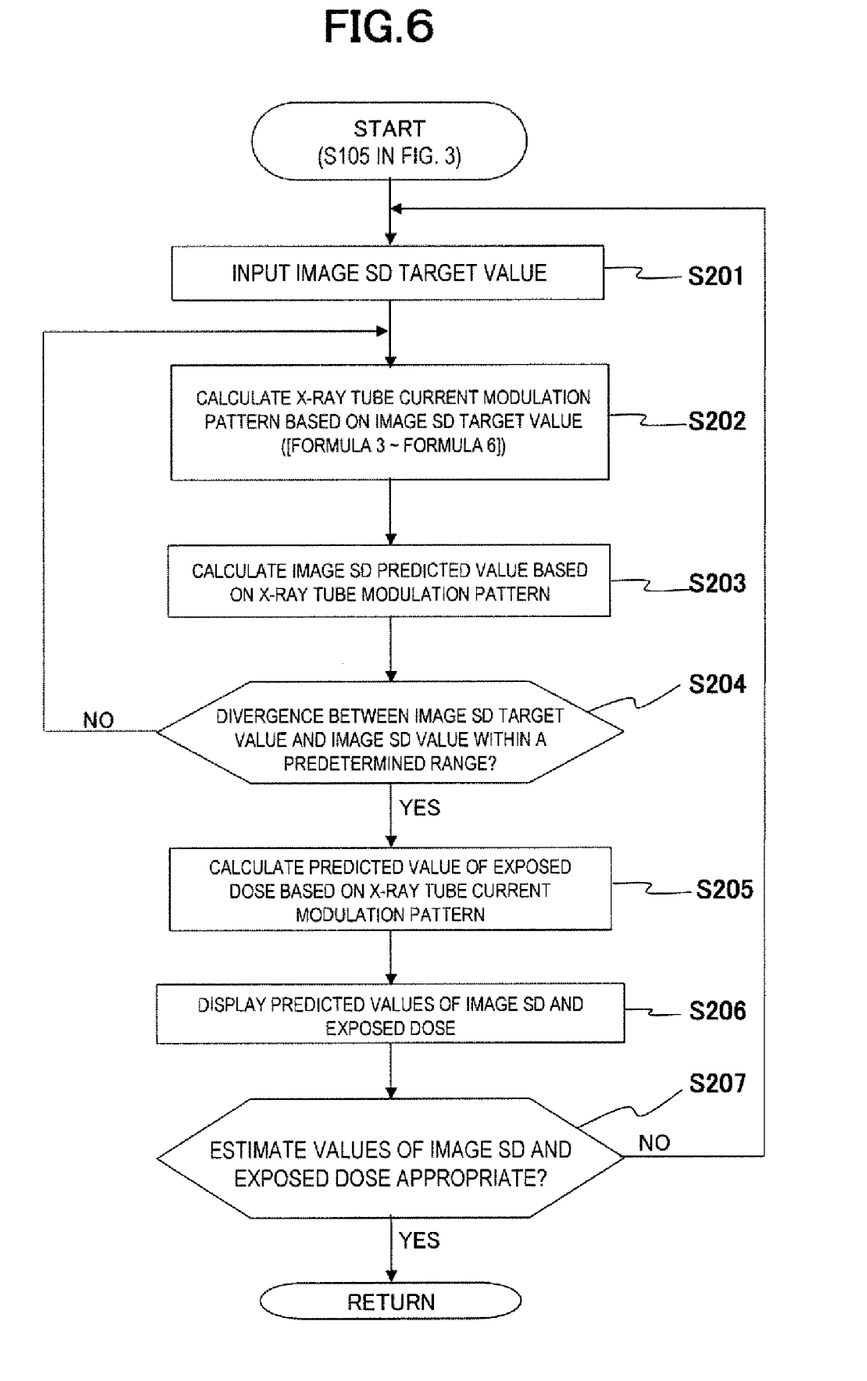
FIG. 6 is a flowchart showing the detail on the calculation of an X-ray tube current modulation pattern.

FIG. 6 is a flowchart showing the detail in calculation of X-ray tube current modulation pattern.

The operator inputs an image SD target value (image noise target value) as an image quality target using operation device 8 (step 201). X-ray CT apparatus 1 stores the inputted image noise target value in storage device 24.

X-ray CT apparatus 1 calculates the X-ray tube current modulation pattern based on the image SD target value (step 202). Concrete calculation formulas ([formula 3]~[formula 6]) of the X-ray tube current modulation pattern will be described later on.

X-ray CT apparatus 1 calculates the image SD predicted value for each slice position [z] based on the X-ray tube current modulation pattern calculated in the process of step 202 (refer to the subsequent description of [formula 3]) (step 203). X-ray CT apparatus 1, in the case that the divergence amount of an image SD target value and an image SD predicted value is not within a predetermined range (for example, less than 5%) ("NO" in step 204), appropriately modifies proportionality constant [k] (refer to the subsequent description on [formula 4]) by executing feedback process.

X-ray CT apparatus 1 calculates an exposure dose predicted value based on the X-ray tube current modulation pattern (step 205). As for the calculation of the exposure dose predicted value, a common technique (for example, refer to JP-A-2006-116137 [0059]~[0062]) can be used.

X-ray CT apparatus 1 displays the calculated image SD predicted value and the exposure dose predicted value on displayer 7 (step 206). The operator confirms the exposure predicted value and the image SD predicted value displayed on displayer 7, and determines whether the balance between the exposure dose and image quality is appropriate or not (step 207). When the operator determines that the balance is appropriate ("YES" in step 207), X-ray CT apparatus 1 proceeds with the process from step 106 onward in FIG. 3. When the operator determines that the balance is not appropriate ("NO" in step 207), the operator inputs the image SD target value again, and X-ray CT apparatus 1 repeats the process from step 201.

After going through the above-described procedure, CT apparatus 1 calculates the X-ray tube current modulation pattern best suited to the image SD target value inputted prior to the scanning, calculates and displays the image SD predicted value and the exposure dose predicted value based on the calculated X-ray tube current modulation pattern. The operator, when the balance between the image SD predicted value and the exposure dose predicted value is determined as inappropriate, inputs an image SD predicted value again, and CT apparatus 1 calculates the X-ray tube current modulation pattern best suited to the newly inputted image SD target value. This X-ray tube current modulation pattern is stored in storage device 24, sequentially called up by system controller 20 in accordance with the diagnostic region of object 6 upon scanning, and the X-ray tube current is controlled via exposure controller 28 during the scanning.

In this manner, X-ray CT apparatus 1 is capable of executing scan while the balance between image quality and exposure dose are optimized, since the X-ray tube current modulation pattern can be determined which is best suited to the image SD target value inputted prior to the scanning.

The process of step 202 in FIG. 6 is equivalent to the modification process of the X-ray tube current modulation pattern in step 111 of FIG. 3. In this case, the calculation is executed using x_dia(z)_ΔHU(z, T), y_dia(z)_ΔHU(z, T) and modu_ratio(z, T) of [formula 1] and [formula 2] in place of x_dia(z), y_dia(z) and modu_ratio(z) of [formula 3]~[formula 8] respectively.

(4. Calculation Formula of X-ray Tube Current Modulation Pattern)

Figure 7:
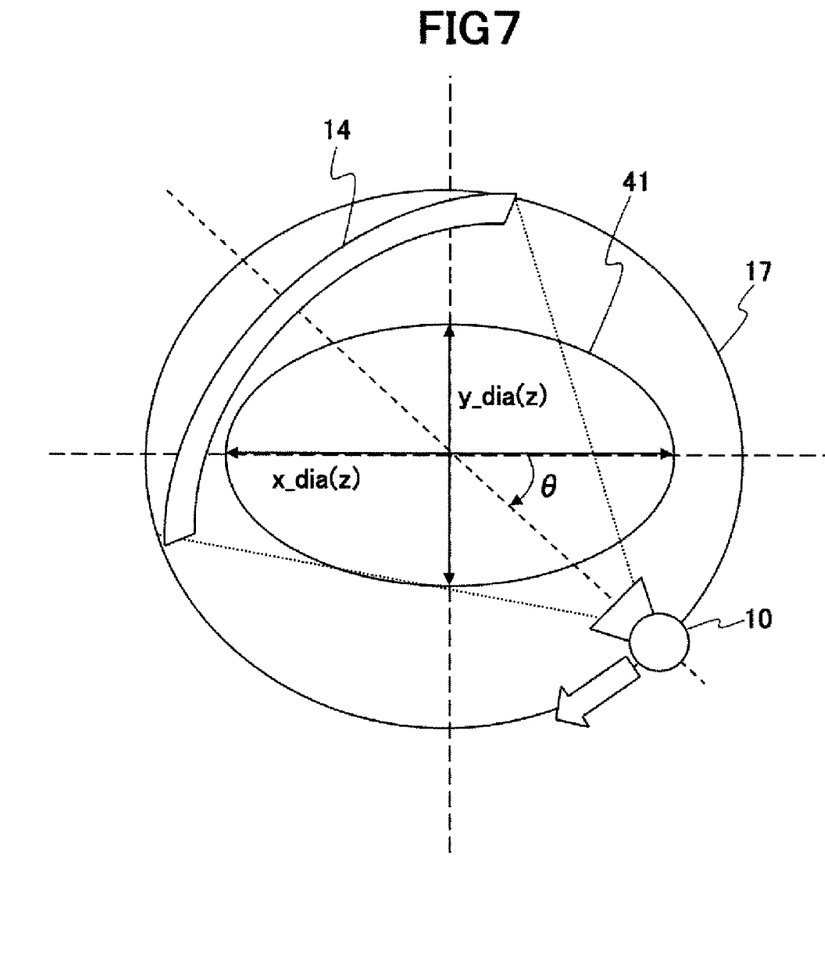
FIG. 7 shows the initial position and rotation direction of X-ray tube 10 with respect to object 3-dimensional model 41 of object 6.

FIG. 7 shows the initial position and the rotation direction of X-ray tube 10 with respect to object 3-dimensional model 41 of object 6.

X-ray CT apparatus 1 calculates the X-ray tube current modulation pattern in accordance with [formula 3]~[formula 6] in the process of step 202 in FIG. 6.

X-ray tube current value [mA_opt(z)] which satisfies image SD target value [SD_tgt(z)] in slice position [z] can be expressed by [formula 3].

$$mA\_opt(z) = mA\_ref * \left(\frac{SD - pred(z)}{SD - tgt(z)}\right)^2 \quad \text{[Formula 3]}$$

In this regard, mA_opt(z): X-ray tube current value, mA_ref(z): reference X-ray tube current value, SD_pred(z): image SD predicted value, and SD_tat(z): image SD target value.

The square of an image SD predicted value is an image SD dispersion predicted value. The image co dispersion predicted value can be calculated using a reference X-ray tube current value. As for the calculation of the image SD dispersion predicted value, a common technique (for example, refer to JP-A-2006-116137 [0052]~[0053]) can be used.

X-ray tube current maximum value [mA_max(z)] in slice position [z] is the X-ray tube current value when X-ray tube 10 is positioned in the long-axis direction of object 3-dimensional model 41, and can be expressed by [formula 4].

$$mA\_max(z) = k * mA\_opt(z) \quad \text{[Formula 4]}$$

In this regard, k: proportionality constant.

The initial value of proportionality constant [k] is stored in storage device 24 in advance. While it is desirable that proportionality constant [k] is appropriately modified by executing feedback process depending on the shape of object 3-dimensional model 41 as shown in step 202~step 204 of FIG. 6, there is no major harm in omitting the process of step 203~step 204.

In slice position [z], X-ray tube current value [mA(θ, z)] when X-ray tube 10 is positioned at X-ray tube phase angle [θ] with respect to object 3-dimensional model 41 can be expressed by [formula 5].

$$mA(\theta, z) = \frac{mA\_max(z)}{2} * \{(1 + modu\_ratio(z)) + (1 - modu\_ratio(z)) * \cos\left(\frac{\pi}{90} * (\theta + \varphi)\right)\} \quad \text{[Formula 5]}$$

In this regard, modu_ratio(z): X-ray tube current attenuation coefficient, when x_dia(z)≧y_dia(z): φ=0, when x_dia(z)<y_dia(z): φ=90, and x_dia(z) and y_dia(z): X-ray transmission length in the long-axis direction or the short-axis direction of object 3-dimensional model 41.

X-ray tube current attenuation coefficient [modu_ratio(z)] indicates the X-ray tube current attenuation ratio based on the maximum X-ray tube current value in slice position [z] depending on the X-ray transmission length, and can be expressed by [Formula 6].

$$modu\_ratio(z) = \exp(-\mu_{kV} * |x\_dia(z) - y\_dia(z)|) \quad \text{[Formula 6]}$$

In this regard, $\mu_{kV}$: a constant set for every X-ray tube voltage. While 0<modu_ratio(z)≦1 is true in theory, the X-ray tube current attenuation ratio can be set appropriately by setting threshold value [modu_ratio_thr] in advance. In this case, modu_ratio_thr<modu_ratio(z)≦1.

Figure 8:
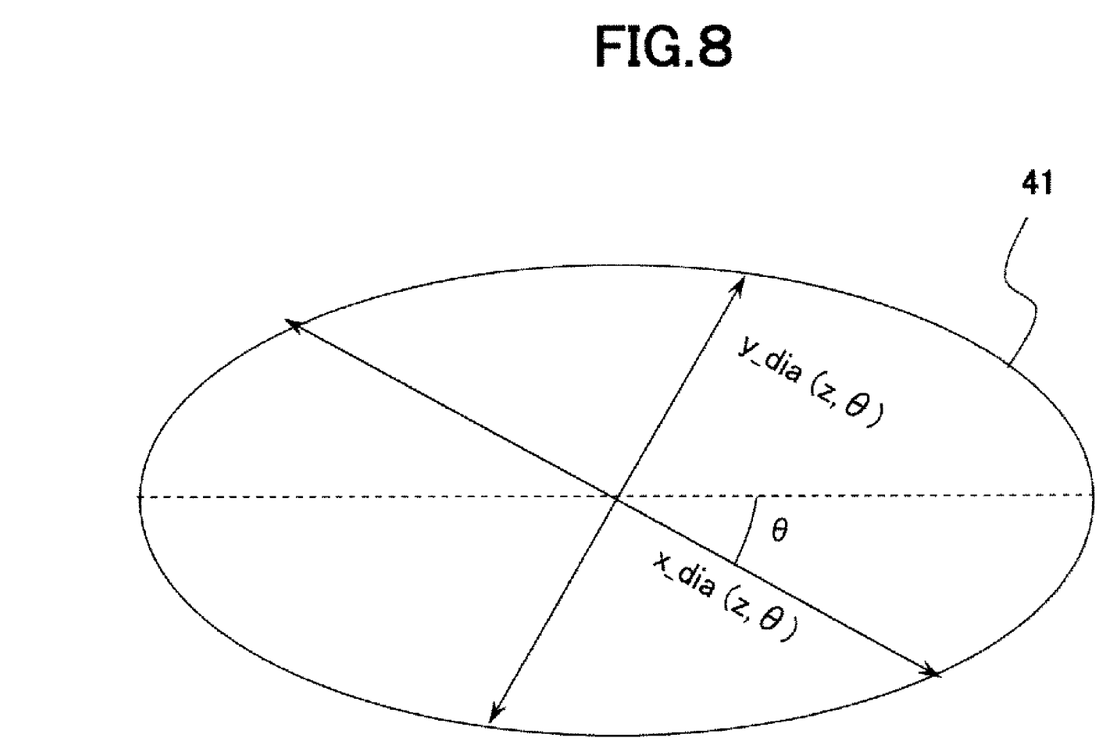
FIG. 8 shows the relationship between the transmission length and the X-ray tube phase angle in object 3-dimensional model 41.

FIG. 8 shows the relationship between the X-ray transmission length and the X-ray tube phase angle in object 3-dimensional model 41.

While the X-ray transmission length in the long-axis or the short-axis direction of object 3-dimensional model 41 is used in [formula 5] and [formula 6], as will be shown in [formula 7] and [formula 8], the X-ray transmission length depending on X-ray tube phase angle [θ] may also be used. Though sufficiently accurate X-ray tube current modulation pattern for practical purpose can be calculated using [formula 5] and [formula 6], the best suited X-ray current attenuation ratio can be set for each view by using [formula 7] and [formula 8] instead.

$$mA(\theta, z) = mA\_max(z) * modu\_ratio(z, \theta) \quad \text{[Formula 7]}$$

$$modu\_ratio(z, \theta) = \exp(-\mu_{kV} * |x\_dia(z, \theta) - y\_dia(z, \theta)|) \quad \text{[Formula 8]}$$

In this regard, modu_ratio(z, θ): the X-ray tube current attenuation coefficient in X-ray tube phase angle [θ], x_dia(z, θ): the X-ray transmission length of object 3-dimensional model 41 in the direction of X-ray tube phase angle [θ], and y_dia(z, θ): the X-ray transmission length of object 3-dimensional model 41 in the direction orthogonal to the direction of X-ray tube phase angle [θ].

Also, while 0<modu_ratio(z, θ)≦1 is true in theory, the X-ray tube current attenuation ratio may be set appropriately by setting threshold value [modu_ratio_thr] in advance. In this case, modu_ratio_thr<modu_ratio(z, θ)≦1.

(5. Calculation of an X-ray Tube Current Modulation Pattern Depending on an X-Ray Tube Voltage)

Figure 9:
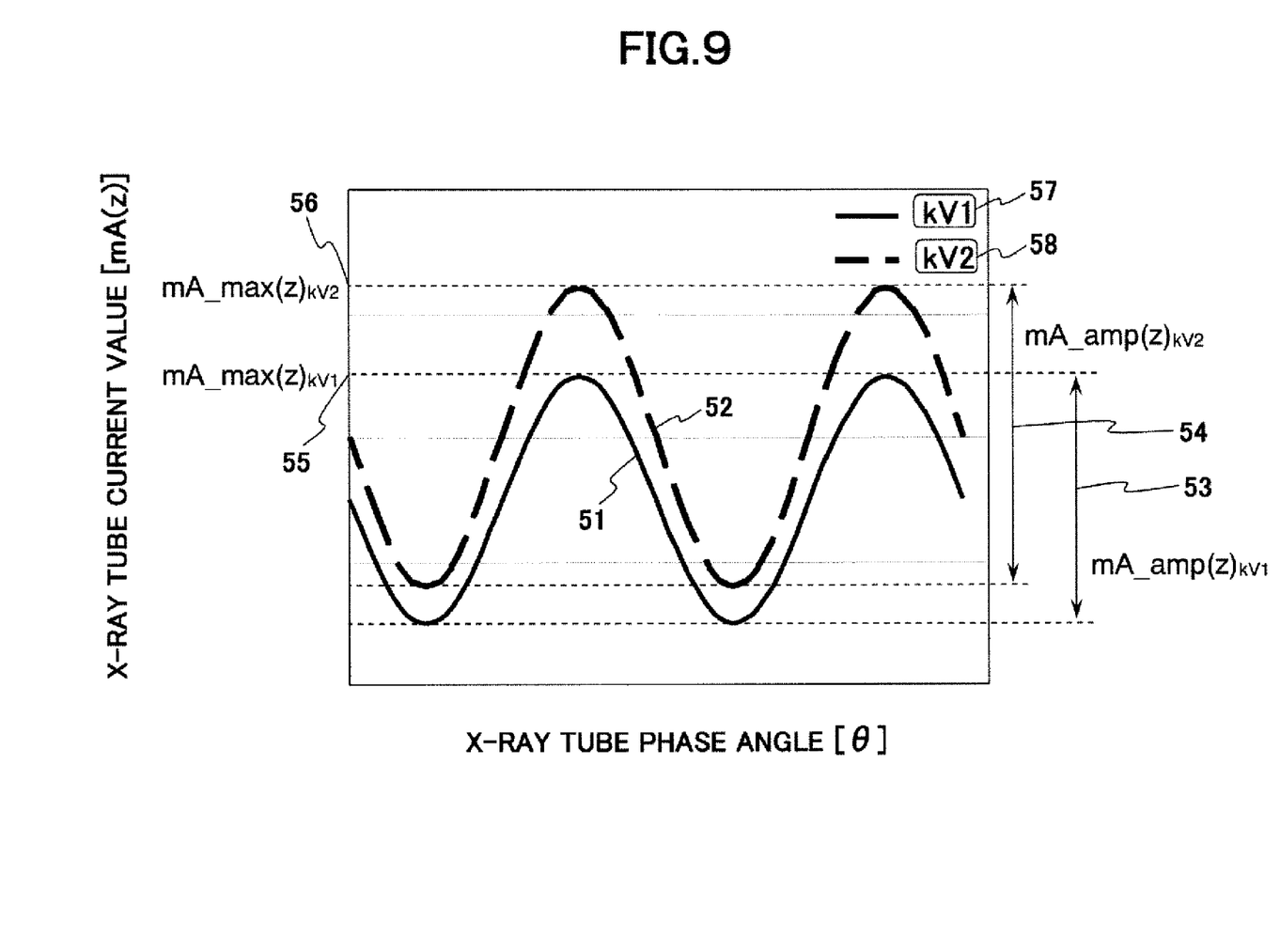
FIG. 9 shows the X-ray tube current modulation pattern in accordance with a X-ray tube current.

FIG. 9 shows an X-ray tube current modulation pattern depending on a tube voltage. It shows the relationship between X-ray phase angle [θ] and X-ray tube current value [mA(z)] in slice position [z] in the case that the X-ray tube voltage is changed.

In accordance with the above-described [formula 3]~[formula 6], in the case that X-ray tube voltage 57[kV1]>X-ray tube voltage 58[kV2], X-ray CT apparatus 1 calculates X-ray tube current modulation pattern 57 with respect to X-ray tube voltage 57[kV1] and X-ray tube current modulation pattern 58 with respect to X-ray tube voltage 58[kV2] under condition that X-ray tube current value amplitude 53[mA_amp(z)$_{kV1}$]<X-ray tube current value amplitude 54[mA_amp(z)$_{kV2}$] and X-ray tube current maximum value 55[mA_max(z)$_{kV1}$]<X-ray tube current maximum value 56[mA_max(z)$_{kV2}$].

In this manner, X-ray CT apparatus 1 is capable of calculating an appropriate X-ray tube current modulation pattern depending on an X-ray tube voltage.

(6. Other Matters)

While the case that X-ray apparatus 1 comprises one X-ray tube 10 is described in the embodiment above, the present invention is applicable to the case that X-ray CT apparatus comprises a plurality of X-ray tubes 10. When X-ray CT apparatus 1 comprises a plurality of X-ray tubes 10, calculation and modification of an X-ray tube current modulation pattern is to be executed for each X-ray tube 10.

While preferred embodiments for the X-ray CT apparatus related to the present invention is described above, no limitation is intended to the examples therein. It is therefore evident to those skilled in the art that the particular embodiments disclosed, above maybe altered or modified without departing from the scope of the technical idea disclosed therein and all such variations are considered within the scope and spirit of the invention.

The invention claimed is:

1. An X-ray CT apparatus comprising:
   an X-ray source configured to irradiate an X-ray while rotating around an object to be examined;
   an X-ray detector disposed facing the X-ray source placing the object therebetween, configured to detect the X-ray dose transmitted through the object;
   image reconstruction means configured to reconstruct a tomographic image of the object based on the detected X-ray dose;
   display means configured to display the tomographic image,
   characterized in further comprising:
   X-ray tube current modulation pattern calculation means configured to calculate the X-ray tube current modulation pattern based on a 3-dimensional model of the object calculated based on a scanogram image of the object;
   start-up shape acquisition means configured to acquire a start-up shape of the CT values or the CT value time difference in a predetermined region of the object after injecting contrast agent into the object;
   time contrast curve prediction means configured to predict a time contrast curve indicating time series variation of the contrast in a diagnostic region of the object with respect to each slice position upon scanning, based on the start-up shape of the acquired CT values or the CT value time difference;
   object 3-dimensional model modification means configured to modify the 3-dimensional model of the object based on the predicted time contrast curve; and
   X-ray tube current modulation pattern modification means configured to modify the X-ray tube current modulation pattern based on the modified object 3-dimensional model.

2. The X-ray CT apparatus according to claim 1, wherein the start-up shape acquisition means acquires a start-up shape of the CT values or the CT value time difference by executing monitoring scan in the upstream position of a diagnostic region of the object.

3. The X-ray CT apparatus according to claim 2, the time contrast curve prediction means has standard data of the time contrast curve, and predicts the time contrast curve by modifying the standard data of the time contrast curve based on information on irradiation condition of the X-ray and/or information on the object.

4. The X-ray CT apparatus according to claim 2, wherein the X-ray tube current modulation pattern calculation means or the X-ray tube current modulation pattern modification means calculates or modifies the X-ray tube current modulation pattern based on the set image target value.

5. The X-ray CT apparatus according to claim 2, wherein the X-ray tube current modulation pattern calculation means or the X-ray tube current modulation pattern modification means determines an X-ray tube current amplitude or an X-ray tube current maximum value based on the X-ray tube voltage to be applied to the X-ray source.

6. The X-ray CT apparatus according to claim 1, the time contrast curve prediction means has standard data of the time contrast curve, and predicts the time contrast curve by modifying the standard data of the time contrast curve based on information on irradiation condition of the X-ray and/or information on the object.

7. The X-ray CT apparatus according to claim 6, wherein the X-ray tube current modulation pattern calculation means or the X-ray tube current modulation pattern modification means calculates or modifies the X-ray tube current modulation pattern based on the set image target value.

8. The X-ray CT apparatus according to claim 6, wherein the X-ray tube current modulation pattern calculation means or the X-ray tube current modulation pattern modification means determines an X-ray tube current amplitude or an X-ray tube current maximum value based on the X-ray tube voltage to be applied to the X-ray source.

9. The X-ray CT apparatus according to claim 1, wherein the X-ray tube current modulation pattern calculation means or the X-ray tube current modulation pattern modification means calculates or modifies the X-ray tube current modulation pattern based on the set image target value.

10. The X-ray CT apparatus according to claim 9, wherein the X-ray tube current modulation pattern calculation means or the X-ray tube current modulation pattern modification means determines an X-ray tube current amplitude or an X-ray tube current maximum value based on the X-ray tube voltage to be applied to the X-ray source.

11. The X-ray CT apparatus according to claim 1, wherein the X-ray tube current modulation pattern calculation means or the X-ray tube current modulation pattern modification means determines an X-ray tube current amplitude or an X-ray tube current maximum value based on the X-ray tube voltage to be applied to the X-ray source.

* * * * *